United States Patent
Romcevich

(10) Patent No.: US 8,968,226 B2
(45) Date of Patent: Mar. 3, 2015

(54) SHRINK-TUBE MEDICAL AND PROTECTIVE DEVICE

(76) Inventor: Nick Romcevich, Longmont, CO (US)

(*) Notice: Subject to any disclaimer, the term of this patent is extended or adjusted under 35 U.S.C. 154(b) by 0 days.

(21) Appl. No.: 13/288,884

(22) Filed: Nov. 3, 2011

(65) Prior Publication Data

US 2013/0116608 A1 May 9, 2013

Related U.S. Application Data

(60) Provisional application No. 61/456,183, filed on Nov. 2, 2010.

(51) Int. Cl.
*A61F 5/00* (2006.01)
(52) U.S. Cl.
USPC ............ 602/6; 602/7; 602/20; 602/23
(58) Field of Classification Search
USPC ............ 602/1, 3, 20–27, 60–65, 75, 6–7; 128/849, 856
See application file for complete search history.

(56) References Cited

U.S. PATENT DOCUMENTS

| | | | |
|---|---|---|---|
| 3,329,143 A * | 7/1967 | Gordon | 602/3 |
| 4,133,924 A | 1/1979 | Seino et al. | |
| 4,346,699 A | 8/1982 | Little et al. | |
| 4,523,586 A | 6/1985 | Couri | |
| 4,552,795 A | 11/1985 | Hansen et al. | |
| 4,665,306 A | 5/1987 | Roland et al. | |
| 4,986,265 A * | 1/1991 | Caponi | 602/3 |
| 5,439,438 A * | 8/1995 | Ersfeld et al. | 602/3 |
| 5,728,052 A * | 3/1998 | Meehan | 602/3 |
| 6,791,003 B1 * | 9/2004 | Choi et al. | 602/48 |
| 8,003,553 B2 | 8/2011 | Fitts, Jr. et al. | |
| 2004/0126518 A1 | 7/2004 | Mendes et al. | |
| 2006/0287623 A1 * | 12/2006 | Beck et al. | 602/3 |
| 2011/0011517 A1 | 1/2011 | Wood | |

FOREIGN PATENT DOCUMENTS

| | | |
|---|---|---|
| CA | 1339055 | 7/1997 |
| DE | 68908303 | 3/1994 |
| EP | 0358451A1 A1 | 3/1990 |
| JP | 2099057 | 4/1990 |

* cited by examiner

*Primary Examiner* — Michael A. Brown
(74) *Attorney, Agent, or Firm* — Stuart J. West; Charlotte Rodeen-Dickert; West & Associates, A PC

(57) ABSTRACT

A therapeutic, supportive, or protective device is fabricated from a material capable of contracting in response to interacting with heat, cold, a chemical reagent, electromagnetic energy, or mechanical energy. The device is positioned over an anatomical joint or other body part and via a "shrink fit," conforms to the part, providing a customizable fit.

8 Claims, 6 Drawing Sheets

SHRINK-TUBE MEDICAL AND PROTECTIVE DEVICE

STATEMENT OF PRIORITY CLAIM

The present application claims priority to U.S. Provisional Patent Application US 61/456,183, filed on Nov. 3, 2010, the contents of which is incorporated herein by reference in its entirety.

BACKGROUND

1. Field of the Invention

The present invention relates to the field of therapeutic and protective devices, particularly those related to anatomical joints and other body parts.

2. Background

In sports, recreational and therapeutic settings, athletic tape, bandages and braces are used to cover anatomical parts in order to provide support and protection. For example, gymnasts may tape their wrists for added support, and boxers may apply athletic tape to their hands and fingers for added padding. Football players may tape their fingers for abrasion protection or to improve grip. Tennis players may wear a knee brace to support their joint during rapid movements, and rugby players may wear elbow sleeves to protect them from multiple impacts. Furthermore, physical therapists may use stretchable bandages or plastic cling wrap to adhere a bag of ice to an ailing body part of a patient. Athletic tape, bandages and braces may also used to cover the anatomical parts or body parts of animals (e.g., horses, dogs, etc.)

Protective and supportive coverings are used in non-therapeutic applications as well. For example, mechanics may wear gloves to protect their knuckles from scrapes and scratches while performing car maintenance but prefer to have their fingertips exposed for increased feel.

Other devices, such as athletic tape, elastomeric wraps, and neoprene sleeves have been used for these application, but can have shortcomings. For example, athletic tape can be difficult to apply to achieve the desired support. Neoprene sleeves, although they have some elasticity, cannot provide a customizable fit and can slip and cause discomfort. The support and/or compression provided by an elastomeric wrap can be somewhat adjusted, by the amount of tension applied to the material, but this can be difficult to control. Further, elastomeric supports can lose their elasticity, and therefore their effectiveness.

"Heat-shrink" tubing is a product used extensively in electrical work to insulate wires, electrical joints and connections from abrasion and environmental stresses. The tubing is placed over the original wire and heat is applied to the tubing in order to shrink it to the diameter of the covered object.

When using heat to activate a shrinking tube over a body part, however, it would be important to ensure that the shrink-activating temperature is less than the burn temperature of skin. Water heaters are typically set at or below 130 degrees Fahrenheit due to the risk of scalding one's skin. Typical heat-shrink materials can be fabricated to have a specific shrink temperature, which can be below 130 degrees Fahrenheit. Therefore, it is reasonable to expect that heat-shrink material can shrink around a body part without burning the user.

Conversely, "cold-shrink" tubing does not require heating and shrinks when removed from its support structure. Other types of contracting materials can be activated by applying a chemical reagent, ultraviolet light, infrared light, radiation or other stimulus.

By contracting a material around a target anatomy, one can obtain a custom fit. In many therapeutic and protective applications, having a snug, yet comfortable fit is critical to device performance. Slippage of a device can cause discomfort, and a loose fit can diminish the support given by the device. In addition, by varying the thickness and elasticity of a material within a device, one can customize for support, compression, and other desired parameters as well.

Shrink tubing has many of the same advantages that tape, braces and bandages have, without many of their disadvantages. Shrink tubing is inexpensive, easy to apply, conforms around the body part, is waterproof, can be treated with adhesives or lubricants, is easy to remove, stays fixed in place, is orthopedically supportive, and provides a protective layer.

What is needed is a disposable, customizable sleeve or wrap fabricated from a "shrink" material that can be quickly and easily applied to support, treat, or protect a joint or other body part.

DETAILED DESCRIPTION

Figure 1:
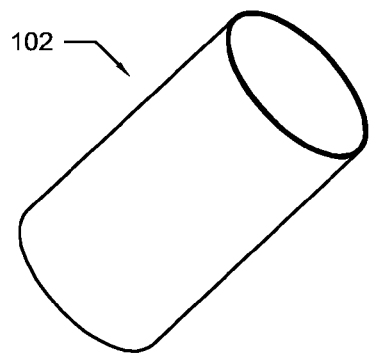
FIG. 1 depicts a perspective of view of one embodiment of the present device.

FIG. 1 depicts a perspective of view of one embodiment of the present device. A sleeve 102 can have a substantially cylindrical geometry, which can be open at at least one end. However, in other embodiments, a sleeve 102 can have any other known and/or convenient geometry. As shown in FIG. 1, the ends can be of substantially the same circumference, but in other embodiments can differ so as to produce a taper along the length of a sleeve 102. In some embodiments, the geometry of such a taper can correspond to the natural taper of a leg, arm, finger, knee, or any other desired target anatomy.

In some embodiments, a sleeve 102 can be made of a polymeric material capable of contracting in at least one direction by an application of an activating modality. An activating modality can be a change in temperature, such as that created by applying heat or cold to the material. A polymeric material can include thermoplastics, thermosets, elastomers, thermoplastic elastomers, thermoset elastomers, or any other known and/or convenient material. In some embodiments, the level of cross-linking in the polymeric material can vary in any known and/or convenient manner or be selected to suit desired properties in the device. In other embodiments, a polymeric material can contract in response to application of a chemical reactant or any other known and/or convenient substance as an activating modality. In other embodiments, a polymeric material can contract in response to application of electromagnetic energy, mechanical energy or any other known and/or convenient form of energy as an activating modality. In such embodiments, a sleeve 102 can contract to conform to a body part and provide a customized fit. In some embodiments, such as those made of a "cold-shrink" material, a support structure can be used within a sleeve 102 to maintain the device in an expanded state.

In some embodiments, a polymeric material can have an elastic modulus in the range 0.05-15 MPa, but in other embodiments can have an elastic modulus in any other known and/or convenient range. In some embodiments, a polymeric material can have a hardness value in the range of Shore A 30-90, but in other embodiments can have a hardness value in any other known and/or convenient range. In some embodiments, a polymeric material can have a set temperature in the range of 0-60 degrees Celsius, but in other embodiments can have a set temperature in any other known and/or convenient range compatible with use in contact with anatomical parts. In some embodiments, a polymeric material can have a shrink ratio in the range of 3:2 to 5:1, but in other embodiments can have a shrink ratio in any other known and/or convenient range.

In some embodiments, a polymeric material can have stable material properties when subjected to various conditions. A polymeric material can demonstrate structural integrity and resistance to environmental factors when subjected to humidity, damp, cold, heat, pressure variations, radiation exposure, flames and any other environmental factors. In addition, in some embodiments, a polymeric material can inherently be or further treated to resist damage from biological factors, such as, but not limited to fungi and bacteria.

In some embodiments, a polymeric material can have various properties to enhance the physical performance of the present device. In some embodiments, a polymeric material can have varying degrees of surface roughness, tackiness, or smoothness to vary the coefficient of friction when the present device is in use. For example, in embodiments of the present device used on finger joints, a polymeric material can have a tacky surface to improve grip. In addition, a polymeric material can have a substantially long shelf-life, which can be on the order of several years, or any other known and/or convenient duration, substantially odorless, and recyclable. Further, in some embodiments, a polymeric material can be predetermined as hydrophobic or hygroscopic as desired for a particular application. For example, in embodiments used in an aquatic environment, hydrophobic properties can be desired.

In other embodiments, a polymeric material can have particular optical properties to enhance aesthetics or for functional purposes. For example, a polymeric material can be substantially transparent or translucent to permit visualization of the target anatomy underneath. In other embodiments, a polymeric material can have reflective properties or specularity for a matte appearance. For examples, in an embodiment where the present device is in use as a knee support, reflectivity can provide a measure of safety to a person running at night while wearing the present device.

In some embodiments, a polymeric material can have other properties related to the production of the polymer itself. The manufacturing of the material may require conventional polymer forming techniques, such as varied cross-linking, using additives, using strands such as glass, molding or expanding a shape, or varying wall thickness in a predetermined manner so as to achieve a desired recovered state of the tube or wrap.

Figure 1A:
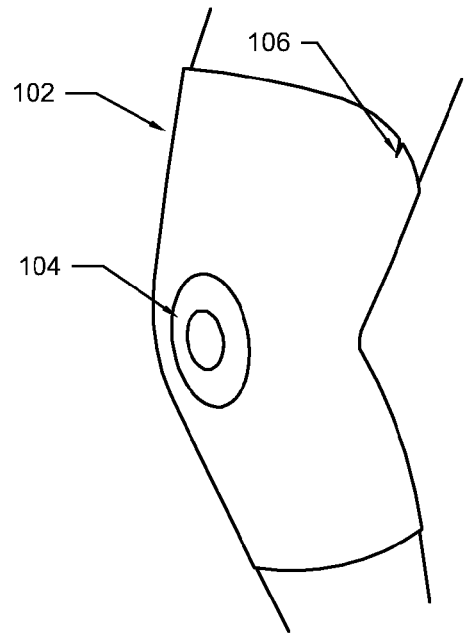
FIG. 1a depicts a perspective of view of one embodiment of the present device in use on a knee.

FIG. 1a depicts a perspective of view of one embodiment of the present device in use on a knee. In some embodiments, a sleeve 102 can have at least one fenestration 104 in its surface to accommodate an anatomical feature. For example, in the embodiment shown in FIG. 1a, a fenestration 104 can accommodate the patella of a knee for more comfort. In other embodiments, a fenestration 104 can be a slit or opening of any other known and/or convenient geometry to allow for variable support or flexure. Similarly, a rib or embossed feature can be added to alter support or flexure attributes. In other embodiments, patterns of fenestrations 104 can change the mechanics or fit of a sleeve 102.

As shown in FIG. 1, a sleeve 102 can have a notch 106 located at any known and/or convenient point along the edge of at least one open end. In some embodiments, a notch 106 can have a triangular geometry, being widest at the edge and converging to an apex at a point slightly below the edge, but in other embodiments can be a uniform slit or any other known and/or convenient geometry. In these embodiments, a notch 106 can provide a defect point in the device to facilitate cutting or tearing it away for removal.

Figure 1B:
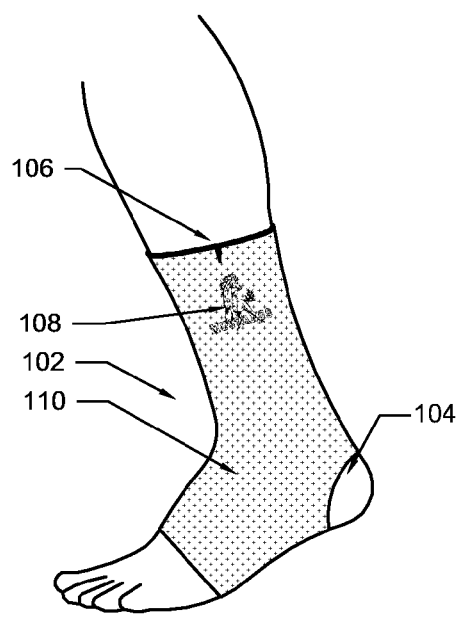
FIG. 1b depicts a perspective of view of one embodiment of the present device in use on an ankle

FIG. 1b depicts a perspective of view of another embodiment of the present device in use on an ankle. In such embodiments, a sleeve 102 can be pre-shaped to accommodate the natural articulation or angle of a joint or other target anatomy. For example, in embodiments designed for use with an ankle, a sleeve 102 can be pre-shaped to be bent at a substantially right angle, or slightly larger or smaller angle at a point along its length. In comparison, in embodiments designed for use on a knee or finger, a sleeve 102 can be substantially straight along its longitudinal axis, or have a slight bend at a point along its length.

In some embodiments, the outer surface of a sleeve 102 can be printed 108 with text, an image, logo, or any other known and/convenient design. In some embodiments, a surface of a sleeve 102 can be textured, which can be aesthetic, but in other embodiments can improve grip. Similarly, perforations may be made in the device to aid in air circulation to cool and dry the covered body part.

Figure 1C:
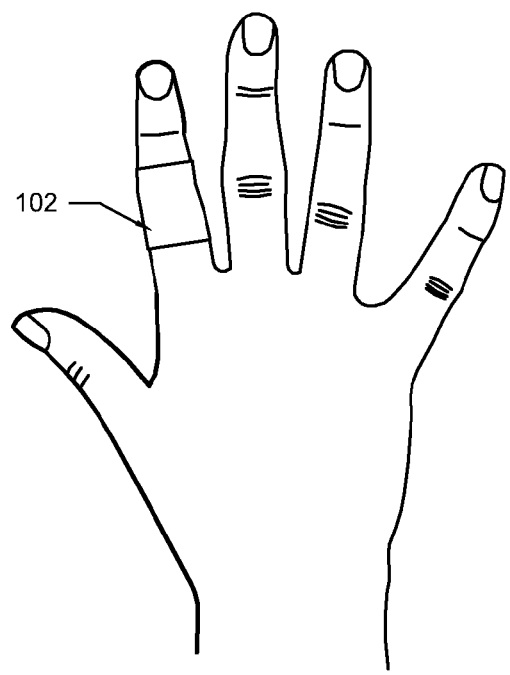
FIG. 1c depicts a perspective of view of one embodiment of the present device in use on a finger.

FIG. 1c depicts a perspective of view of another embodiment of the present device in use on a finger. In some embodiments, the outer surface of a sleeve 102 can be or printed 108 with text, an image, logo, or any other known and/convenient design. In some embodiments, texturing 110 can be aesthetic, but in other embodiments can improve grip. In other embodiments, the device may encapsulate two adjacent fingers to stabilize a jammed or dislocated finger to the opposing healthy finger or an inserted splint. In yet another embodiment, the present device can be closed at one end and applied as a "finger-cot" or thimble.

Figure 2:
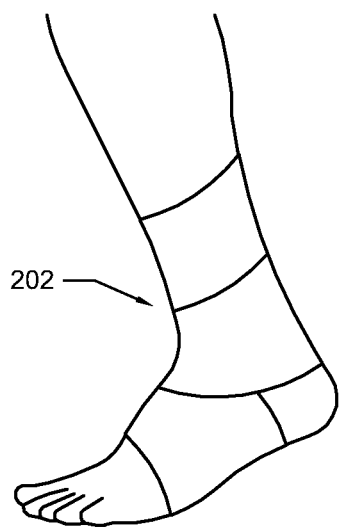
FIG. 2 depicts a perspective of view of a wrap embodiment of the present device in use on an ankle joint.

FIG. 2 depicts a perspective of view of a wrap embodiment of the present device in use on an ankle joint. In such embodiments, an elongated strip 202 can be substantially spirally wrapped around a body part.

Figure 2A:
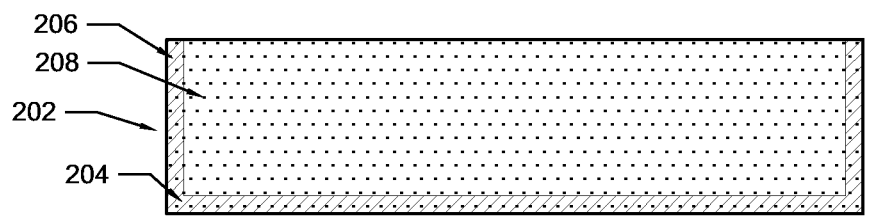
FIG. 2a depicts a planar view of the embodiment shown in FIG. 2 before it is wrapped around an ankle joint.

FIG. 2a depicts a planar view of the embodiment shown in FIG. 2 before it is wrapped around an anatomical joint or other body part. An elongated strip 202 can also be made of a polymeric material capable of contracting in at least one direction by an application of an activating modality. An activating modality can be a change in temperature, such as that created by applying heat or cold to a material. An activating modality can be a change in temperature, such as that created by removing or extracting heat from a material. A polymeric material can include thermoplastics, thermosets, elastomers, thermoplastic elastomers, thermoset elastomers, or any other known and/or convenient material. In other embodiments, a polymeric material can contract in response to application of a chemical reactant, electromagnetic energy, mechanical energy, or any other known and/or convenient stimulus. In such embodiments, a strip 202 can contract to conform to a body part and provide a customized fit. In some embodiments, an elongated strip 202 can have a length-to-width ratio of at least 2:1 and upwards of 100:1, but in other embodiments can have any other known and/or convenient ratio. In the embodiment shown in FIG. 2, an elongated strip 202 can have an adhesive region 204 along at least one edge. In some embodiments, an adhesive region 204 can further comprise a pressure-activated adhesive, a thermal adhesive, or any other known and/or convenient substance, and the adhesive can be distributed across the entire surface area of the device 206. In some embodiments, an adhesive region 204 can be along at least one lateral edge of an elongated strip 202 to assist in holding it in place while wrapping. Second adhesive regions located on at least one of the ends of an elongated strip 202 can anchor the ends of an elongated strip 202 to skin, clothing, or to the elongated strip 202 itself. In some embodiments of the present device, perforations 208 can be made in the surface of an elongated strip 202 or sleeve 102 to improve breathability when the device is in use.

Figure 2B:
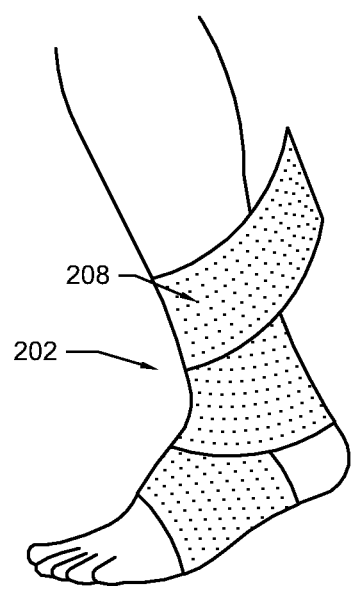
FIG. 2b depicts a perspective view of the embodiment shown in FIG. 2 in use as it is wrapped around a joint.

FIG. 2b depicts a perspective view of the embodiment shown in FIG. 2 in use as it is wrapped around a body part, such as an ankle joint. When being wrapped in a spiral configuration around a body part, the lateral edges of an elongated strip 202 can be aligned adjacent to each other, either in contact with each other or with a gap between the edges, or can be overlapped to any extent desired. In other embodiments, a strip 202 can be placed substantially flat and adjacent to skin, but in a substantially linear or curved geometry, rather than substantially spirally wrapped around a target anatomy.

Figure 3:
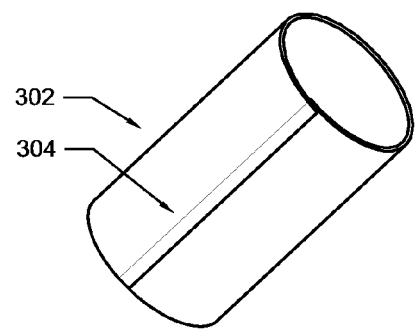
FIG. 3 depicts a perspective view of another embodiment of the present device.

FIG. 3 depicts a perspective view of another embodiment of the present device. In the embodiment shown in FIG. 3, at least one sheet 302 can be wrapped around a body part so as to produce at least one longitudinal seam 304. As shown in FIG. 3, a seam 304 can be produced by an overlap of opposite edges of a sheet 302. However, in other embodiments, as seam 304 can be created by opposite edges contacting each other without an overlap, or by being joined and folded or rolled (i.e., a "flat-felt" seam). In other embodiments, a seam 304 can be created joining opposite edges by a fastener, such as, but not limited to, a hook-and-loop fastener.

Figure 3A:
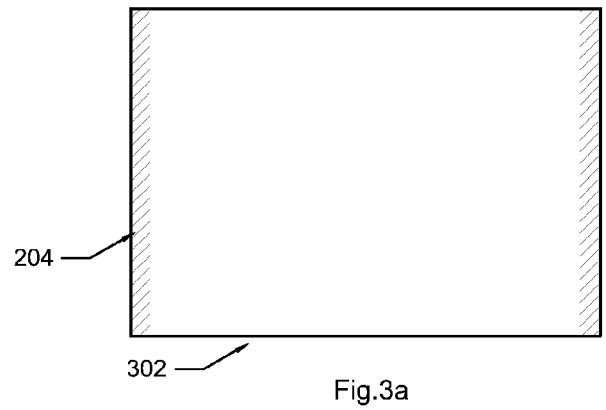
FIG. 3a depicts a planar view of the embodiment shown in FIG. 3.

FIG. 3a depicts a planar view of the embodiment shown in FIG. 3. In some embodiments, a sheet 302 can be substantially rectangular. As shown in the embodiment in FIG. 3a, a planar sheet 302 can have at least one adhesive region 204. In some embodiments, an adhesive region 204 can be located along opposite ends of a sheet 302, but in other embodiments can be located along opposite sides of a sheet 302, or in any other known and/or convenient combination thereof.

Figure 3B:
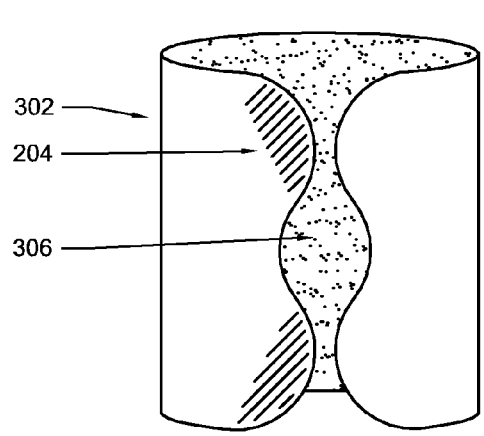
FIG. 3b depicts a perspective view of another embodiment of the device shown in FIG. 3.

However, other embodiments, as shown in FIG. 3b, can have edges shaped to conform to a particular joint or create a fenestration 104 when the edges are joined to form a seam 304. In the embodiment shown in FIG. 3b, the lateral edges can be joined to form a fenestration 104 to accommodate a patella, an elbow, or a heel, for example. In some embodiments, an adhesive region 204 can be at least one of the lateral edges to secure the edges that can form a seam 304. In some embodiments, a device can have one surface coated with an antiseptic, a cooling agent, a heating agent, aloe vera, burn relief, a sanitation agent, healing, or therapeutic substance 306, that when the device is in use, can be in contact with the skin.

A sheet 302 can also be made of a polymeric material capable of shrinking in at least one direction by an application of an activating modality. An activating modality can be a change in temperature, such as that created by removing or extracting heat from a material. A polymeric material can include thermoplastics, thermosets, elastomers, thermoplastic elastomers, thermoset elastomers, or any other known and/or convenient material. In other embodiments, a polymeric material can contract in response to application of a chemical reactant, electromagnetic energy, mechanical energy, or any other known and/or convenient stimulus. In such embodiments, a sheet 302 can shrink to conform to a body part and provide a customized fit.

Figure 3C:
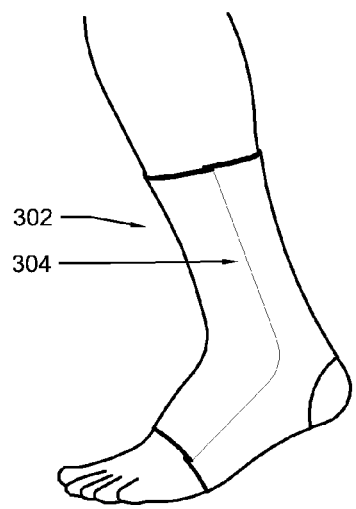
FIG. 3c depicts a perspective view of the embodiment shown in FIG. 3 after it is wrapped around and conformed to an ankle joint.

FIG. 3c depicts a perspective view of the embodiment shown in FIG. 3 after it is wrapped around and conformed to an ankle joint by shrinkage of the material. In some embodiments, a seam 304 can be aligned on a lateral side, but in other embodiments, can be positioned in any other known and/or convenient location.

Figure 4:
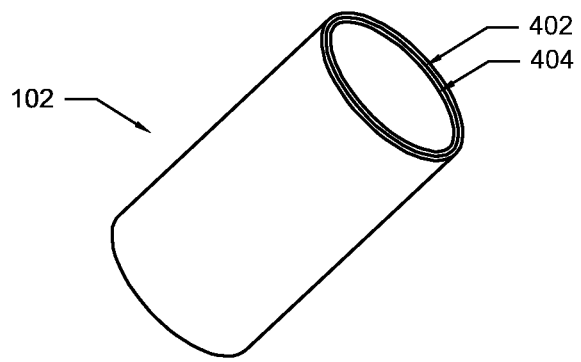
FIG. 4 depicts a perspective view of another embodiment of the present device having a layered construction.

FIG. 4 depicts a perspective view of another embodiment of the present device having a layered construction. In some embodiments, a sleeve 102 can have a plurality of layers 402. When in use, one of the layers 402 can be an inner layer 404 adjacent to the skin. In such embodiments, an inner layer can be comprised of fabric, polymer, gel, or any other known and/or convenient material. In some embodiments, an inner layer 404 can be continuous or further comprised of separate pieces. This layered substance may also be an integrated gauze pad, cloth piece, foam strip, bandage, or antiseptic pad used to cover a cut, wound burn, needle puncture site, or other lesion. Additionally, the outer surface may be treated or may integrate a layer of alternate material, such as a soft material like velvet or fleece, for use when wiping off sweat or wiping a runny noise using a covered hand.

Figure 5:
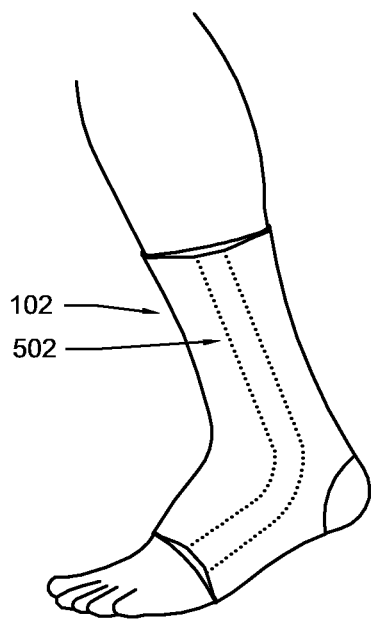
FIG. 5 depicts a perspective view of another embodiment of the present device having regions of varying thicknesses in use on an ankle joint.

FIG. 5 depicts a perspective view of another embodiment of the present device having regions of varying thicknesses in use on an ankle joint. As shown in FIG. 5, in some embodiments a sleeve 102 can further comprise at least one thickened region 502. For example, in use on an ankle or a knee, a sleeve 102 can have thickened regions 502 substantially along the lateral sides to provide additional support, rigidity, flexure, padding, cushioning, and/or protection. In embodiments used on a finger joint, a thickened region 502 can provide additional support, cushioning, and/or protection for the top of a knuckle. In other embodiments a strip 202 and a sheet 302 can also further comprise at least one thickened region 502. In some embodiments, the wall thickness of the sleeve 102 can vary along the length of the axis to provide different shrink rates and stiffness for improved functionality.

Figure 6:
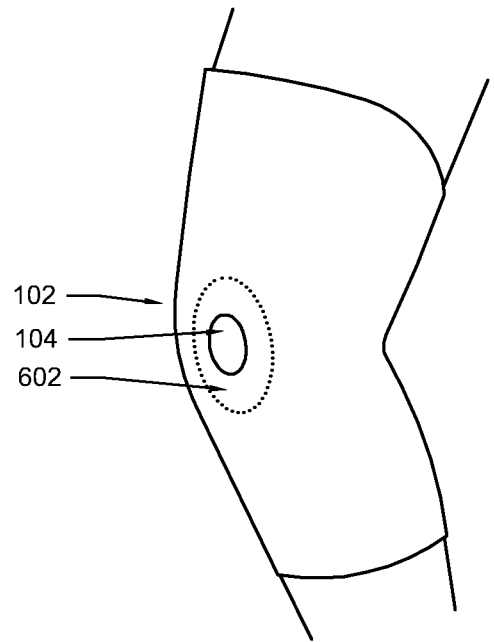
FIG. 6 depicts a perspective view of another embodiment of the present device having regions of different materials in use on a knee joint.

FIG. 6 depicts a perspective view of another embodiment of the present device having regions of different materials in use on a knee joint. In the embodiment shown in FIG. 6, a sleeve 102 can have a region of a different (e.g. having a different elastic modulus, texture, or any other known and/or convenient characteristic,) material 602. In some embodiments, a region of thinner material 602 can coincide with a fenestration 104. For example, as shown in FIG. 6, a region of thinner material 602 can be located within a fenestration 104 configured to accommodate a patella. However, in other embodiments, a region of thinner material 602 can be located at any other known and/or convenient position on a sleeve 102, strip 202, or sheet 302.

Figure 7:
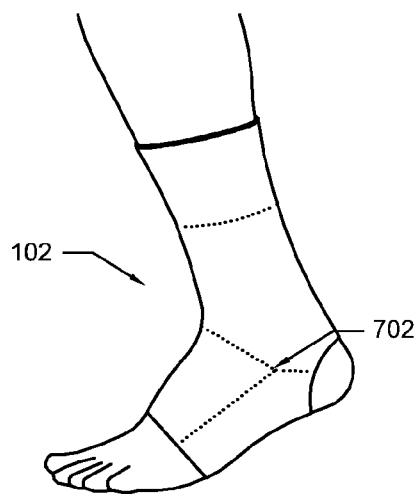
FIG. 7 depicts a perspective view of another embodiment of the present device having regions of different material properties in use on an ankle joint.

FIG. 7 depicts a perspective view of another embodiment of the present device having regions of different material properties in use on an ankle joint. In the embodiment shown in FIG. 7, a sleeve 102 can be further comprised of regions having different material properties 702. In some embodiments regions of different material properties 702 can be further comprised of either one material having altered properties or of different materials having different properties.

Regions of different material properties 702 can provide specific areas of compression, support, cushioning, protection, minimize slipping, and improve fit and comfort for the wearer. Controlling site-specific compression can promote rapid healing, lessened pain and reduced swelling due to the restriction of blood flow. Additionally, the device can be used as an insulating garment to provide warmth in specific areas, such as a skier having a wrap around his wrist to cover the junction between the gloves and jacket sleeve.

Figure 8:
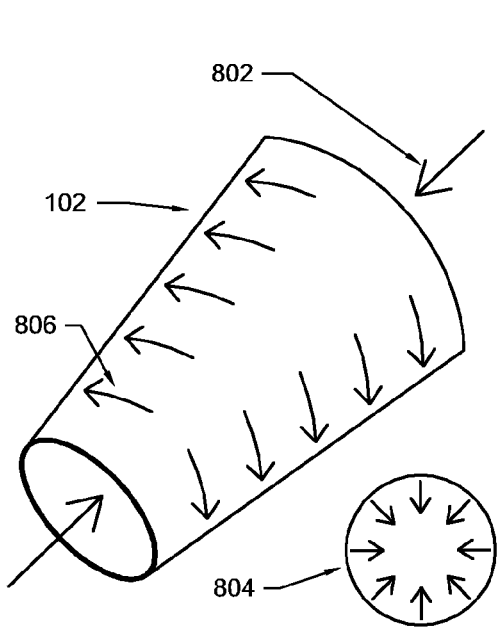
FIG. 8 depicts a perspective view of another embodiment of the present device showing the directions of material contraction.

FIG. 8 depicts a perspective view of another embodiment of the present device showing the directions of material contraction. In some embodiments, a sleeve 102, or a strip 202 wrapped spirally, 802 and a sheet 302 wrapped around a body part into a substantially cylindrical configuration can contract along a longitudinal axis and/or in an internally radial direction 804, and/or a substantially circumferential direction 806. By contracting in an internally radial direction 804, a sleeve 102, or a strip 202 wrapped spirally, and a sheet 302 wrapped around a body part into a substantially cylindrical configuration can conform to a body part to provide a custom fit. A sleeve 102, strip 202, and/or sheet 302 can conform to a body part by reducing an effective circumference of sleeve 102, strip 202, and/or sheet 302. In some embodiments, an effective circumference of a portion, section, or part of a sleeve 102, strip 202, and/or a sheet 302 can be reduced. An effective circumference of a portion, section, or part can be reduced such that one portion of sleeve 102, strip 202, and/or sheet 302 can conform more closely to a body part than another portion. An amount of reduction in circumference may be controlled or determined by controlling a level of application of heat, cold, a chemical reactant, electromagnetic energy, mechanical energy, or any other known and/or convenient stimulus. By varying the contraction of the material by the application of heat, cold, a chemical reactant, electromagnetic energy, mechanical energy, or any other known and/or convenient stimulus, varying degrees of support can be obtained.

Figure 9:
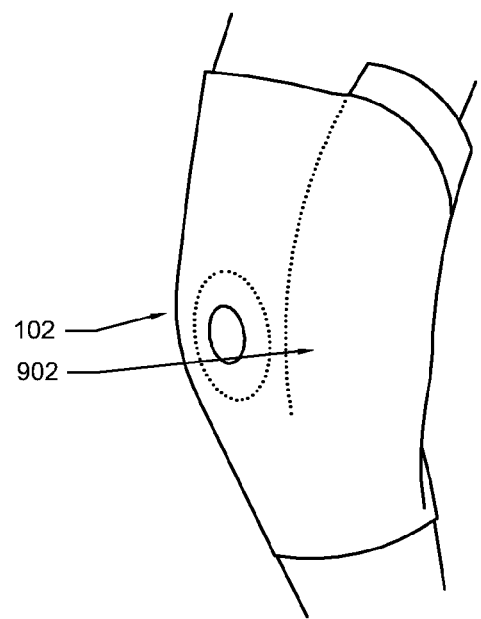
FIG. 9 depicts a perspective view of another embodiment of the present device used in conjunction with a thermal modality.

FIG. 9 depicts a perspective view of another embodiment of the present device used in conjunction with a thermal modality. In some embodiments, a separate thermal modality 902 can be used in conjunction with a sleeve 102, strip 202, or sheet 302. In such embodiments, a separate thermal modality 902 can be an ice bag, heat pack, chemical cold pack, a fluid circulating pad, or any other known and/or convenient device. A separate thermal modality 902 can be first applied to a body part and then surrounded by a sleeve 102, strip 202, or sheet 302, which is then contracted, holding a separate thermal modality in place. In some embodiments, in which a sleeve 102, strip 202, or sheet 302 can be contracted by the application of heat or cold, a separate thermal device 902 can also activate contraction by coming into contact with the material of a sleeve 102, strip 202, or sheet 302.

Figure 10:
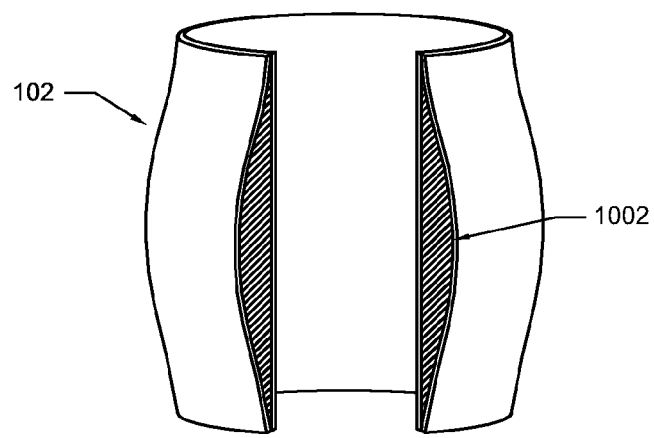
FIG. 10 depicts a perspective cutaway view of another embodiment the present device having an integrated thermal modality.

FIG. 10 depicts a perspective cutaway view of another embodiment of the present device having an integrated thermal modality. In some embodiments, a sleeve 102, strip 202, or sheet 302 can further comprise an integrated thermal modality 1002. In such embodiments, an integrated thermal modality 1002 can be an ice bag, heat pack, chemical cold pack, a fluid circulating pad, or any other known and/or convenient device. A sleeve 102, strip 202, or sheet 302 can be applied to a body part such that it surrounds an integrated thermal modality 1002 that can be in contact with a body part or positioned on the outer surface of a sleeve 102, or a strip 202 wrapped spirally and a sheet 302 wrapped around a body part into a substantially cylindrical configuration. In some embodiments, in which a sleeve 102, strip 202, or sheet 302 can be contracted by the application of heat or cold, an integrated thermal modality 1002 can also activate contraction by coming into contact with the material of a sleeve 102, strip 202, or sheet 302.

Figure 11:
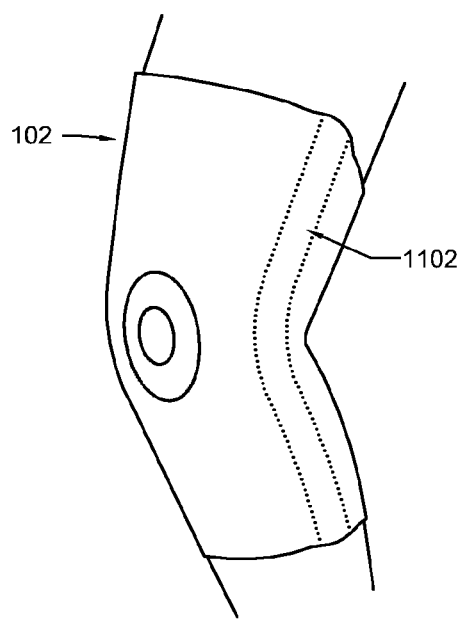
FIG. 11 depicts a perspective cutaway view of another embodiment the present device having integrated rigid support structures in use on a knee joint.

FIG. 11 depicts a perspective cutaway view of another embodiment of the present device having additional support structures in use on a knee joint. In the embodiment shown in FIG. 11, a sleeve 102, or a strip 202 wrapped spirally, and a sheet 302 wrapped around a body part into a substantially cylindrical configuration can further comprise at least one additional support structure 1102. As shown in FIG. 11, a support structure 1102 can be an elongated member of length corresponding to the length of the lateral side of a joint. In some embodiments, such as those designed to be used in conjunction with a knee, at least one support structure 1102 can be positioned along the longitudinal and/or lateral joint line to restrict joint movement in that direction. In embodiments designed to be used in conjunction with an ankle, a support structure 1102 can be positioned over at least one lateral side of an ankle. In other embodiments designed to be used in conjunction with an ankle, a support structure 1102 can be a "stirrup" extending around the bottom of the heel and covering both lateral sides of an ankle. Another embodiment can be a splint to be used to stabilize a finger or an articulating rod system running down the side of a knee brace to control twisting of a joint. In some embodiments, a support structure 1102 can be made of a polymer, metal, or any other known and/or convenient material.

Figure 12:
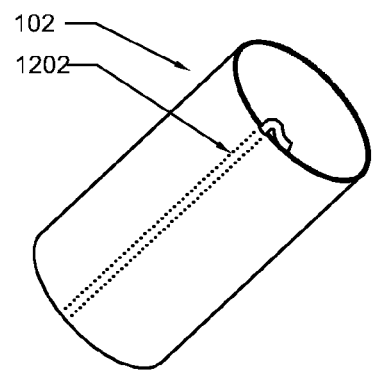
FIG. 12 depicts a perspective view of another embodiment the present device having a pull-cord removal device.

FIG. 12 depicts a perspective view of another embodiment the present device having a pull-cord removal device. As shown in FIG. 12, a sleeve 102, or a strip 302 wrapped spirally and a sheet 302 wrapped around a body part into a substantially cylindrical configuration can further comprise a cord 1202 to facilitate removal of the present device. In some embodiments, a cord 1202 can have a substantially circular cross-section, but in other embodiments can be flattened or have any other known and/or convenient geometry. In some embodiments, a cord 1202 of length substantially commensurate with the length of a sleeve 102 can be positioned longitudinally along the interior surface of a sleeve 102 such that a portion of a cord 1202 can extend slightly above an edge of a sleeve 102. In other embodiments, a cord 1202 of length substantially commensurate with the length of a strip 202 can be positioned longitudinally along the interior surface of a strip 202 such that when a strip 202 is wrapped around a body part, a portion of a cord 1202 can extend slightly past the end of a strip 202. In other embodiments, a cord 1202 of length substantially commensurate with the length of a sheet 302 can be positioned longitudinally along the interior surface of a sheet 302 such that when a sheet 302 is wrapped around a body part, a portion of a cord 1202 can extend slightly above an edge of a sheet 302.

In some embodiments, the present device can be used in the following methods. A material capable of contraction can be fashioned into a sleeve 102, strip 202, or sheet 302. A sleeve 102 can be of a a geometry capable of substantially surrounding a body part, while a strip 202 or sheet 302 can be fashioned into a geometry capable of substantially surrounding a body part. A person can position a sleeve 102, or configured strip 202 or sheet 302 to substantially surround a body part, such as a finger joint or other anatomical region. Initially, a sleeve 102 can be of an interior effective diameter to such that it can fit loosely around a body part. In other embodiments, a wrap 202 or a sheet 302 can be positioned to substantially surround or encapsulate a target anatomy. A material of an embodiment of the present device (e.g., sleeve 102, strip 202, sleeve 302 or other material) can be activated (e.g., using an activation modality) to contract about body part (e.g., finger, knee, elbow, ankle or any other body part or anatomical region) and conform to the body part. When custom fit to the targeted body part, a sleeve 102, strip 202, or sheet 302 can provide many desired effects including, but not limited to, anatomical support or coverage during physically strenuous activities or provide thermal, blunt-force or abrasion resistance during repetitive manual tasks. In some embodiments, the compression provided to the targeted anatomy can promote rapid healing, and reduced pain and swelling due to the restricted blood flow to the site. Once a sleeve 102, wrap 202, or sheet 302 is no longer needed, it can be removed by tearing or cutting a sleeve 102, wrap 202, or sheet 302 at a notch 106, or by pulling a cord or strip 1202, and can be disposed or recycled.

In other embodiments, the present device (e.g. an anatomical support device, a protective device, decorative body-art device, insulating device or other device) can have many medical and other applications. An anatomical device can, for example, also be a decorative body-art device, protective device, insulating device or other device. In some embodiments, the present device can be used in conjunction with therapeutic and pharmaceutical substances in the treatment of burns or other dermatological conditions. In other embodiments, the present device can provide lubrication coating. In other embodiments, the present device can provide decorative uses, such as, but not limited to team colors or logos. The present device can also have embodiments used in conjunction with or used itself as thermally insulating garments. In some embodiments, the present device can also be used as a foundation garment.

"Shrink" material offers many of the same advantages that tape, braces and bandages have, without many of their disadvantages. Shrink material can be inexpensive, easy with which to work, and can be capable of conforming around the body part to achieve a custom fit. Shrink material can also be waterproof and can be treated with adhesives or lubricants. Shrink material can be fashioned into an embodiment of the present device that can be easy to remove, can stay fixed in place, can be orthopedically supportive, and can provide a protective layer. Further, embodiments of the present device can be disposable, customizable, and quickly and easily applied to support, treat, or protect a target anatomy.

In some embodiments, the present device can be made of a polymeric material capable of contracting in at least one direction by applying heat to the material. In such embodiments, heat can be applied by conduction, convection or radiation. For example, in some embodiments, heated air can be applied with a conventional hair dryer, or any other known and/or convenient device. In other embodiments, heat can be applied with direct contact from an external heated unit, such as a heating pad. In other embodiments, heat can be applied by surrounding the device with a heated fluid, such as water. As heat is applied, the present device can contract to conform to the surrounded body part, the fit and structure of the present device can be controlled. In some embodiments further comprising a thermal modality 902 1002, heat can be applied to the present device with activation of a thermal modality 902 1002. Upon cooling to a desired temperature, which can be approximately 20 degrees Celsius ("room temperature"), an ambient temperature, or any other known and/or convenient temperature, the present device can maintain the shape of the surrounded body part to provide, support, compression, and/or protection.

In some embodiments, the present device can be made of a polymeric material capable of contracting in at least one direction by applying cold to the material. In such embodiments, cold can be applied by conduction or convection. For example, in some embodiments, cooled air can be applied with a conventional hair dryer, or any other known and/or convenient device. In other embodiments, cold can be applied with direct contact from an external cold unit, such as a cooling pad. In other embodiments, cold can be applied by surrounding the device with a cooled fluid, such as water. As cold is applied, the present device can contract to conform to the surrounded body part. By varying the temperature and duration of the applied cold, the fit and structure of the present device can be controlled. In some embodiments further comprising a thermal modality 902 1002, cold can be applied to the present device with activation of a thermal modality 902 1002. Upon returning to ambient temperature, the present device can maintain the shape of the surrounded body part to provide, support, compression, and/or protection. In some embodiments, a "cold-shrink" material can exhibit compressing over time (creeping) as opposed to it being necessary to "treat" with cold temperatures. Further, "cold-shrink" materials can recover to the inactivated state over a potentially variable timeframe, such that a repeated application of cold may be necessary.

In some embodiments, the present device can be made of a polymeric material capable of contracting in at least one direction by applying a chemical reagent to the material. In such embodiments, a reagent can be applied via a liquid, gel, aerosol, or any other know and/or convenient substance. For example, in some embodiments, a chemical reagent can be applied by wiping, immersing, coating, spraying, and or any other known and/or convenient method. As a chemical reagent is applied, the present device can contract to conform to the surrounded body part. By varying the concentration and duration of exposure of the material to the chemical reagent, the fit and structure of the present device can be controlled. Upon completion of the reaction, the present device can maintain the shape of the surrounded body part to provide support, compression, and/or protection.

In some embodiments, the present device can be made of a polymeric material capable of contracting in at least one direction by applying a form of electromagnetic energy to the material. In such embodiments, energy can be applied visible light, ultraviolet light, infrared light, or any other know and/or convenient energy. For example, in some embodiments, electromagnetic energy can be applied by illuminating the material or any other known and/or convenient method. As energy is applied, the present device can contract to conform to the surrounded body part. By varying the intensity and duration of exposure of the material to the energy, the fit and structure of the present device can be controlled. Upon completion of the reaction, the present device can maintain the shape of the surrounded body part to provide support, compression, and/or protection.

In some embodiments, the present device can be made of a polymeric material capable of contracting in at least one direction by applying a form of mechanical energy to the material. In such embodiments, energy can be applied ultrasonic waves or any other know and/or convenient mechanical energy. For example, in some embodiments, ultrasonic waves can be applied to the material by an ultrasonic emitter any other known and/or convenient device. As mechanical energy is applied, the present device can contract to conform to the surrounded body part. By varying the intensity and duration of exposure of the material to the mechanical energy, the fit and structure of the present device can be controlled. Upon completion of the reaction, the present device can maintain the shape of the surrounded body part to provide support, compression, and/or protection.

Although the invention has been described in conjunction with specific embodiments thereof, it is evident that many alternatives, modifications and variations will be apparent to those skilled in the art. Accordingly, the invention as described and hereinafter claimed is intended to embrace all such alternatives, modifications and variations that fall within the spirit and broad scope of the appended claims.

What is claimed is:

1. A therapeutic anatomical device, comprising:
   a sleeve having a substantially cylindrical geometry with at least one end open, and having a thickness adequate to provide an elastic section modulus to resist a bending moment sufficient to restrict the normal range of motion of an anatomical part absent significant deformation;
   wherein said sleeve is comprised of an elastomeric, dermatologically compatible material capable of contraction upon exposure to an activation modality, and wherein said contraction causes an effective reduction in circumference of at least a portion of said sleeve to conform to and support a target anatomy;
   wherein said activation modality is selected from the group consisting of: heat cold, chemical reagent, electromagnetic energy, mechanical energy;
   further comprising;
   at least one region having a greater thickness than that of the sleeve;
   and an integrated therapeutic member;
   wherein said therapeutic member is a longitudinal support member; and
   wherein said therapeutic member is at least one lateral support brace.

2. The device of claim 1, wherein said therapeutic member is a cushion.

3. The device of claim 2, wherein said cushion is comprised of a gel-based material.

4. The device of claim 2, wherein said cushion is comprised of a polymeric material.

5. The device of claim 1, further comprising at least one fenestration in a surface of said sleeve.

6. The device of claim 1, further comprising a therapeutic substance.

7. The device of claim 6, wherein said therapeutic substance is an analgesic.

8. The device of claim 1, further comprising an integrated activation modality.

* * * * *